United States Patent
Pedro Santos Manso Côrte-Real et al.

(10) Patent No.: US 9,832,366 B2
(45) Date of Patent: Nov. 28, 2017

(54) FOCUSING METHOD

(71) Applicant: BIOSURFIT S.A., Aveiro (PT)

(72) Inventors: José Pedro Santos Manso Côrte-Real, Lisbon (PT); Francisco Correia De Matos Nolasco Lamas, Lisbon (PT)

(73) Assignee: Biosurfit, S.A., Aveiro (PT)

( * ) Notice: Subject to any disclaimer, the term of this patent is extended or adjusted under 35 U.S.C. 154(b) by 0 days.

(21) Appl. No.: 15/515,498

(22) PCT Filed: Sep. 29, 2015

(86) PCT No.: PCT/EP2015/072416
§ 371 (c)(1),
(2) Date: Mar. 29, 2017

(87) PCT Pub. No.: WO2016/050767
PCT Pub. Date: Apr. 7, 2016

(65) Prior Publication Data
US 2017/0223262 A1 Aug. 3, 2017

(30) Foreign Application Priority Data

Sep. 29, 2014 (GB) .................................. 1417170.6
Sep. 29, 2014 (PT) .................................... 107932 U

(51) Int. Cl.
*H04N 5/232* (2006.01)
*G02B 21/24* (2006.01)
(Continued)

(52) U.S. Cl.
CPC ........... *H04N 5/23212* (2013.01); *G02B 7/38* (2013.01); *G02B 21/244* (2013.01);
(Continued)

(58) Field of Classification Search
CPC ............. H04N 5/23212; H04N 5/2226; G02B 21/367; G02B 21/244; G02B 21/247;
(Continued)

(56) References Cited

U.S. PATENT DOCUMENTS 5,932,872 A * 8/1999 Price .................... G01N 15/147
250/201.3
7,538,815 B1 * 5/2009 Belikov ................... G02B 7/36
348/345
(Continued)

FOREIGN PATENT DOCUMENTS

EP 0 468 100 A1 1/1992
EP 2 439 511 A1 4/2012
(Continued)

OTHER PUBLICATIONS

PCT International Search Report and Written Opinion for PCT/EP2015/072416, dated Jan. 4, 2016, 13 pgs.
(Continued)

*Primary Examiner* — Roberto Velez
*Assistant Examiner* — Tuan Le
(74) *Attorney, Agent, or Firm* — Patterson Thuente Pedersen, P.A.

(57) ABSTRACT

A method and system are provided for focusing an imaging device on a liquid sample flowing through a field of view of the imaging device. Objects are segmented in the captured frames and used to account for the fact that the sample is flowing. Object velocities are calculated and used in selecting an appropriate focus value. The calculation of a focus measure takes account of the number of objects in captured frames in order to ensure a consistent calculation of the focus measure.

27 Claims, 2 Drawing Sheets

(51) Int. Cl.
*G02B 7/38* (2006.01)
*G02B 27/00* (2006.01)
*G02B 27/40* (2006.01)
*G02B 7/28* (2006.01)

(52) U.S. Cl.
CPC ......... *G02B 27/0075* (2013.01); *G02B 27/40* (2013.01); *G02B 7/28* (2013.01)

(58) Field of Classification Search
CPC .................................. G02B 7/36; G02B 21/26; G06T 2207/10056; G06T 2207/30004
See application file for complete search history.

(56) References Cited

U.S. PATENT DOCUMENTS

| | | | |
|---|---|---|---|
| 8,808,312 B2 * | 8/2014 | Rioux | A61B 17/0469 600/37 |
| 8,988,520 B2 * | 3/2015 | Liu | G02B 21/367 348/355 |
| 9,470,618 B2 * | 10/2016 | Farrell | G01N 15/1468 |
| 2004/0217256 A1 | 11/2004 | Ortyn et al. | |
| 2009/0237665 A1 | 9/2009 | Wardlaw et al. | |
| 2010/0308205 A1 * | 12/2010 | Chang | G02B 21/365 250/201.3 |
| 2011/0157344 A1 | 6/2011 | Xie et al. | |
| 2012/0013727 A1 | 1/2012 | Breniman et al. | |
| 2012/0135874 A1 * | 5/2012 | Wang | C12Q 1/6844 506/9 |
| 2012/0157160 A1 | 6/2012 | Ozcan et al. | |
| 2013/0100272 A1 | 4/2013 | Price et al. | |
| 2014/0273067 A1 | 9/2014 | Wanders et al. | |

FOREIGN PATENT DOCUMENTS

| | | |
|---|---|---|
| WO | WO 96/22556 A1 | 7/1996 |
| WO | WO 2004/092781 A2 | 10/2004 |

OTHER PUBLICATIONS http://www.researchgate.net/publication/239398674_An_Isotropic_3_3 Image_Gradient_Operator Feb. 2014, 6 pages.

* cited by examiner

FOCUSING METHOD

RELATED APPLICATIONS

This application is a National Phase entry of PCT Application No. PCT/EP2015/072416, filed Sep. 29, 2015, which claims priority from Great Britain Application No. 1417170.6, filed Sep. 29, 2014, and which claims priority from Portuguese Application No. 107932 U, filed Sep. 29, 2014, the disclosures of which are hereby incorporated by referenced herein in their entirety.

FIELD OF THE INVENTION

The present invention relates to a method and system for focusing an imaging device on a liquid sampling flowing through a field of view of the imaging device.

BACKGROUND OF THE INVENTION

Many different algorithms are known for focusing imaging devices. It would be desirable to have a robust and efficient focusing algorithm specifically adapted for focusing on a flowing liquid sample.

SUMMARY OF THE INVENTION

Aspects of the invention are set out in the independent claims. Optional features of embodiments of the inventions are set out in the dependent claims, dependent thereon.

In some embodiments, there is provided a method of focusing an imaging device on a liquid sample flowing through a field of view of the imaging device. A focus mechanism of the imaging device is stepped through a plurality of focus values while capturing frames of a sample containing objects as the same flows through the field of view of the imaging device. Objects in the captured frames are segmented and a focus measure is determined for each focus value from the captured frames. Object velocities of at least one object in at least some of the frames are determined. One of the plurality of focus values is selected based on the determined focus measures and object velocities and the focus mechanism is set using the selected focus value.

Advantageously, by using the knowledge that objects in the flowing sample are moving, the selection of a focus value that corresponds to a focus plane in which the sample flows (objects move) is facilitated by considering object velocities in the selection of the focus value.

In some embodiments, selecting a focus value involves selecting a focus value for which the corresponding focus measure is a local extremum and the corresponding object velocity is larger than object velocities at any other local extrema of the determined focus measures. For example, candidate focus values at which the focus measure is at an extremum may be determined and the candidate focus value selected for which a corresponding object velocity determined from frames captured with that focus value is largest. In this way, focus values corresponding to a focus plane having a large focus measure due to artefacts such as a scratch in a cover glass can be distinguished from a focus value corresponding to a focus plane containing the moving objects and hence the flowing sample. Other selection criteria are used in some embodiments, for example the corresponding object velocity exceeding a threshold. By suitable selection of the threshold, it can be ensured that the object velocity associated with the selective focus value is larger than object velocity at any other of the local extremum of the focus measures. The object velocity associated with a given focus value may be the maximum, minimum, average, median or other ensemble measure of the respective object velocities of objects captured at that focus value, or an object or object velocity may be selected from all the objects/object velocities of objects captured at that focus value, at random or in accordance with a predetermined criterion.

In some embodiments, determining a focus measure for each focus value involves determining the focus measure using image patches around the segmented objects such that the magnitude of the focus measure is independent of the number of objects in each frame. For example, the focus measure may be determined using an average of respective focus measures calculated for each object captured while the focus mechanism is set to that focus value. In some embodiments, a maximum, minimum, median or other ensemble measure is used instead of the average. All or a subset of the segmented objects may be used for this calculation. In some other embodiments, an object/image patch is selected from the objects captured at each focus value, randomly or based on a predetermined criterion. In some embodiments, the focus measure for an image is calculated over the whole image and normalised by a detected number of objects. Thus, more generally, the focus measure for an image may be calculated such that it is independent of the number of objects in the image.

In some embodiments, the focus measure is a contrast-based focus measure. For example, a Sobel operator may be used to derive the focus measure by convoluting the operator with captured pixels. See for example http://www.researchgate.net/publication/239398674_An_Isotropic_3_3_Image_Gradient_Operator. For example, focus measures may be calculated by convoluting the operator with image patch or patches around segmented objects. In other embodiments, the operator is applied to the whole image. Other operators may also be used to calculate the focus measure, as is well known in the art.

Advantageously, by calculating focus measures on a per patch/patch averaged basis, the effect of a varying number of objects present in any one captured frame of the flowing sample does not affect the comparison of the focus measures between frames. Hence the corresponding variation of the overall image contrast is accounted for.

In some embodiments, the selected focus value is refined by stepping the focus values through a plurality of focus values around the selected focus value. The refined focus value is used to set the focus mechanism. In some embodiments, respective focus measures are calculated for each of the plurality of focus values around the selected focus value and the refined focus value is chosen to be that for which the corresponding focus measure is largest (more generally indicating best focus). In these embodiments, setting the focus mechanism using the selected focus value involves refining the focus value as described and using the refined focus value to set the focus mechanism.

Advantageously, the described refinement procedure allows the focus value to be fine-tuned. In some embodiments, the above steps are repeated to obtain a plurality of selected focus values, with or without refinement. In some embodiments, only the refinement is repeated. The resulting selected (or refined) focus values are combined to find a final focus value for setting the focus mechanism, for example by averaging, taking the median or another ensemble measure.

BRIEF DESCRIPTION OF THE FIGURES

A specific embodiment is now described, by way of example only, with reference to the accompanying drawings, in which.

DETAILED DESCRIPTION OF THE INVENTION

Figure 1:
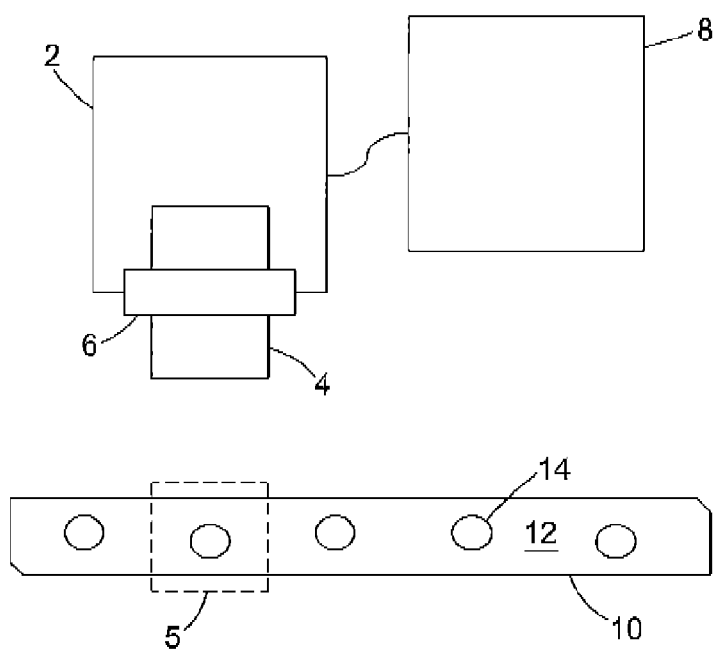
FIG. 1 is a schematic illustration of an imaging device for imaging a flowing sample.

With reference to FIG. 1, an imaging device 2 comprises an objective (lens) assembly 4 for forming an image of a field of view 5 inside the imaging device 2. A focusing mechanism 6 is coupled to the objective assembly 4 to move the objective assembly along an optical axis in order to focus at a given depth inside the field of view. A focus value is a value indicative of where the imaging device 2 is focused. The focus value may be chosen to be a position along the optical axis of the objective assembly 4 relative to the imaging device 2, a distance of an imaged plane in focus from the imaging device 2, a value related to the configuration of the focus mechanism (e.g. rotor position of a focus drive motor) or any other value indicative of where the imaging device is focused.

A processor 8 is coupled to the imaging device 2 and receives images and other signals for processing from the imaging device 2. In turn, the processor sends control information to the imaging device 2, including control information to set a focus value and cause the focus mechanism 6 to position (or configure) the objective assembly 4 in accordance with the focus value, as well as to, in some embodiments, control one or more other parameters of the imaging device, for example the imaging gain of an image sensor inside the imaging device 2. It will be understood that the imaging device 2 and processor 8 may be provided as separate units or may be housed in a single unit. For example, components of the processor 8 and imaging device 2 may be provided on a single integrated circuit.

A sample conduit 10 carries a flowing sample 12 containing objects 14. For example, the sample may be a blood sample and the objects may be blood cells, for example white blood cells. The sample conduit 10 is disposed within the field of view 5, so that the sample 12 and objects 14 can be imaged by the imaging device, for example capturing a time series of frames at a given sample rate. The sample conduit 10 is disposed fixedly relative to the imaging device 2 in a manner not illustrated in FIG. 1 for clarity. The sample 10 and imaging device 2 may form part of a single device or, for example, the sample conduit 10 may be provided on a microfluidic analysis cartridge which can be inserted into a holder associated with the imaging device 2 to fixedly dispose the sample conduit 10 relative to the imaging device 2. In some embodiments, the sample conduit 10 is provided on a disk cartridge implementing a lab on a disk device and the imaging device and processor it may be part of a DVD reader like reader device including a mechanism for loading the lab on a disk device. Flow of the sample may be driven by a variety of driving mechanisms, including capillary forces, centrifugal forces, electrophoretic forces and any other suitable driving mechanisms.

Figure 2:
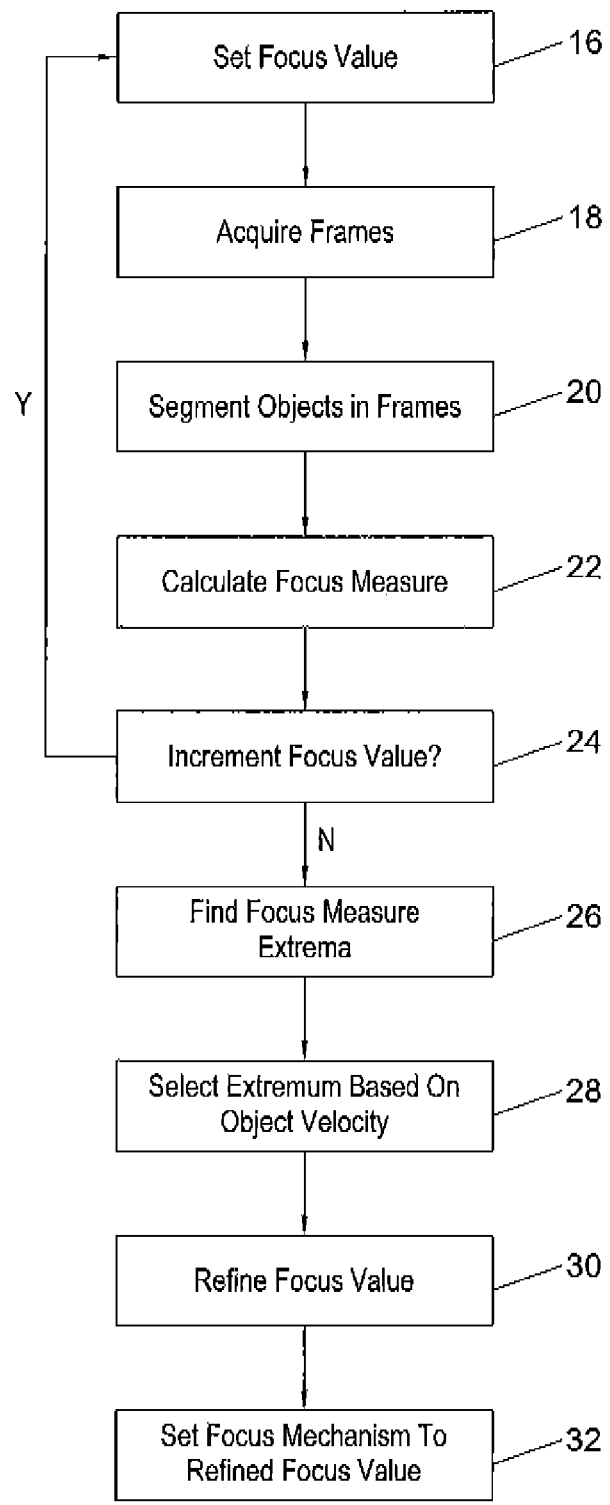
FIG. 2 is a flow diagram of a method of focusing an imaging device such as illustrated in FIG. 1.

With reference to FIG. 2, a process for focusing the objective assembly 4 using the focus mechanism 6 and processor 8 is now described.

At step 16, the processor sets a focus value that causes the focusing mechanism to the position the objective assembly 4 accordingly. Subsequently, at step 18, frames acquired by the imaging device are received by the processor and objects in the acquired frames are segmented at step 20 in accordance with known techniques for image segmentation.

At step 22, a focus measure is acquired, associated with the set focus value. An image patch is defined around each segmented object and a Sobel operator is convoluted with each image patch. The results of these convolutions are averaged over image patches to calculate the focus measure for the said focus value.

In a specific implementation, the following Sobel operator and magnitude calculation is used to derive an average gradient magnitude as a focus measure for each image patch:

If each image patch is denoted by A, and Gx and Gy define two images patches which at each point contain the horizontal and vertical derivative approximations, the computations are as follows:

$$G_x = \begin{bmatrix} -1 & 0 & +1 \\ -2 & 0 & +2 \\ -1 & 0 & +1 \end{bmatrix} * A \text{ and } G_y = \begin{bmatrix} +1 & +2 & +1 \\ 0 & 0 & 0 \\ -1 & -2 & -1 \end{bmatrix} * A$$

where * denotes a 2-dimensional convolution operation.

At each pixel in the image, the resulting gradient approximations can be combined to give the gradient magnitude as the square root of the sum of the squares of Gx and Gy at the pixel, or the sum of the absolute values as an approximation. This quantity is then averaged or summed over the image patch pixels to give the focus measure.

At step 24, the processor determines whether a desired number of focus value/measurement pairs have been obtained or whether further pairs need to be obtained. If further pairs are needed, the process loops back to step 16 after the focus value is incremented for example by adding a constant step size or looking up the next focus value in a set of focus values. If the preset number of pairs has been acquired, the focus value is not incremented further but the process proceeds to step 26.

At step 26, local extrema of the focus measure as a function of focus values are found. The skilled person will be familiar with many ways of finding local extrema, one example being a hysteris threshold algorithm. In case that the focus measure increases with increasing quality of focus, the extrema will be maxima and in the case that the focus measure decreases with focus quality, the extremer will be minima. Thus, the extrema are always local maxima of focus (focus quality, focus sharpness, etc.).

If, at step 26, only a single extrema is found, the process jumps to step 30, described in more detail below. If a plurality of focus measure extrema are found, the process proceeds to step 28 and one of the extrema is selected. A plurality of focus extrema may arise, for example, when dust particles on an outer surface of the sample conduit 10, an air bubble on an inner surface of the sample conduit 10 and possibly a scratch on a opposed outer surface form additional image planes with high contrast features in addition to an image plane containing the objects 14 in the sample 12 flowing in the sample conduit 10. Only the latter is the plane in which the focus should be placed. This plane can be distinguished from the others in that the objects in question, flowing in the sample, are moving. Therefore, the desired object plane can be identified on the basis of the velocity of the objects in which the focus measures were calculated.

Accordingly, at step 28, object velocity is calculated from the frames associated with each pair of focus values/focus measure. Ways of calculating object velocities of objects in captured images are well known. For example, for an object detected in a first frame, it is checked whether there is a single object within a detection radius from the position of the object in the first frame in the next frame. If so, these objects are taken to correspond to the same physical object and a velocity is calculated using the difference between the object positions in the two frames and the sample rate. If more than one object is detected in the radius in the subsequent frame, the calculation for that object is aborted. An overall object velocity is then determined by averaging individual object velocities determined for the relevant frames as described. The extremum (focus value/measurement pair) associated with the highest average object velocity is then selected for subsequent use in focusing (setting the focus mechanism 42).

At step 30, the selected focus value from step 26 or step 28 is used as a starting point for focus refinement. A set of focus values around the selected focus value is defined, for example a pre-set number of values each side of the selected value with a given step width. The step width will be smaller than the step width of the increment at step 24, so that the focus value search at steps 16 to 24 represents a coarse initial search and the set of focus values defined at step 30 represent a fine search around the focus value found with the coarse search. Similar to steps 16 to 24, the processor controls the focus mechanism to step through the set of focus values and acquires frames at each focus value to calculate corresponding focus measures. The focus value of this set of focus values that has the highest/best focus measure is then determined and used at step 32 by the processor to set the focus mechanism to that value.

It will be appreciated that a specific embodiment has been described by way of illustration only and that various modifications, alterations and juxtapositions of the described features are possible without departing from the invention, as described above and otherwise. In particular, the steps of the process described above with reference to FIG. 2 can to some extent be changed in order and may be grouped and combined as appropriate. Frames may be captured and received as needed at each step or frame acquisition may be ongoing with only those frames used that are relevant. Where appropriate, step sequences described above may be interchanged for corresponding batch processes, for example steps 16, 18 and 24 may be grouped as a batch process to provide sets of frames associated with corresponding focus values and segmentation of objects and calculation of focus measures may be done as a further batch process.

The described processes can be implemented using any suitable stand-alone or distributed computing environment using any suitable computing platform or processor, for example an integrated circuit, self-contained or in combination with other components of the system, a dedicated computing device housed on an appropriate card together with the other components of the system or otherwise, a standalone computing device such as a personal computer, tablet computer or mobile phone or a server which performs the necessary processes at least in part remotely exchanging data over a network connection.

The invention claimed is:

1. A method of focusing an imaging device on a liquid sampling flowing through a field of view of the imaging device, the method comprising:
   stepping a focus mechanism of the imaging device through a plurality of focus values while capturing frames of the sample as the sample flows through a field of view of the imaging device;
   segmenting objects within the sample in the captured frames;
   determining a focus measure for each focus value from the captured frames;
   determining object velocities of at least one object in at least some of the frames;
   selecting one of the plurality of focus values based on the determined focus measures and object velocities; and
   setting the focus mechanism using the selected focus value.

2. A method as claimed in claim 1, wherein selecting one of the plurality of focus values comprises selecting a focus value for which the corresponding focus measure is a local extremum and a corresponding object velocity is larger than object velocities at any other local extremum of the determined focus measures.

3. A method as claimed in claim 1, wherein determining a focus measure comprises determining the focus measure such that the magnitude of the focus measure is independent of the number of objects in each frame.

4. A system for focusing an imaging device on a liquid sample flowing through a field at view of an imaging device, the system comprising:
   an imaging device; and
   a processor con tired to carry out the method steps of claim 1.

5. A non-transitory computer program product comprising coded instructions with, when run on a processor, implement a method as claimed in claim 1.

6. A non-transitory computer readable storage medium or media comprising a program product as claimed in claim 5.

7. A method of focusing an image device on a liquid sample flowing through a field of view of the imaging device, the method comprising:
   stepping a focus mechanism of the imaging device through a plurality of focus values while capturing frames of the sample as the sample flows through a field of view of the imaging device;
   segmenting objects within the sample in the captured frames;
   determining a focus measure for each focus value from the captured frames such that the magnitude of the focus measure is independent of the number of objects in each frame;
   selecting one of the plurality of focus values based on the determined focus measures; and
   setting the focus mechanism using the selected focus value.

8. A method as claimed in claim 7, the method comprising refining the selected focus value by setting the focus mechanisms to a plurality of focus values around the selected focus value, determining respective focus measures, selecting a refined focus value based on the respective focus measures and using the refined focus value to set the focus mechanism.

9. A method of focusing an imaging device on a liquid sample flowing through a field of view of the imaging device, the method comprising:
   a) stepping a focus mechanism of the imaging device through a plurality of focus values;
   b) acquiring at least one video frame at each of the plurality of focus values using the imaging device;
   c) calculating a focus measure for each of the plurality of focus values from the respective at least one video frame;
   d) selecting a plurality of respective focus values substantially at local extrema of the focus measure;

e) for each selected focus value, determining a respective object velocity for one or more objects in a respective plurality of frames;
f) selecting a focus value of the plurality of focus values based on each of the respective object velocities; and
g) focusing the imaging device using the selected focus value.

10. A method as claimed in claim 9, wherein calculating a focus measure for each focus value includes detecting one or more objects in each respective frame; defining an image patch for each of the one or more objects and calculating the focus measure for at least one of the image patches in the respective frame.

11. A method as claimed in claim 10, wherein calculating a focus measure for each focus value includes averaging the torus measure over objects.

12. A method as claimed in claim 9, wherein step g) comprises:
h) stepping the focus mechanism of the imaging device through a further plurality of focus values comprising at least one focus value above and at least one focus value below the selected focus value;
i) acquiring at least one video frame at each of the further plurality of focus values using the imaging device;
j) calculating a focus measure for each of the further plurality of focus values from the respective at least one video frame;
k) selecting a further focus value based on the focus measures for the further plurality of focus values; and
l) focusing the imaging device using the selected further focus value.

13. A method as claimed in claim 12, wherein step l) comprising:
m) repeating steps a) to k) to select at least one more further locus value;
n) combining the further focus values to derive a final focus value, and
o) setting the focus mechanism to the final focus value.

14. A method as claimed in claim 12, wherein a step size between the further plurality of focus values is less than a step size between the plurality of focus values.

15. A method as claimed in claim 9, wherein the sample flows in a microfluidic conduit.

16. An imaging system comprising:
an imaging device for imaging a liquid sampling flowing through a field of view of the imaging device, wherein the imaging device has a focus mechanism for positioning at least a portion of the imaging device in accordance with the focus value to form a focused image of one or more objects in the field of view; and
a processor configured to:
cause the focus mechanism to step through a plurality of focus values while the imaging device captures frames of the sample as the sample flows through the field of view of the imaging device;
segment objects within the sample in the captured frames;
determine a focus measure for each focus value from the captured frames;
determine object velocities of at least one object in at least some of the frames;
select one of the plurality of focus values based on the determined focus measures and object velocities; and
cause the focus mechanism to be set using the selected focus value.

17. A system as claimed in claim 16, wherein selecting one of the plurality of focus values comprises selecting a focus value for which the corresponding focus measure is a local extremum and a corresponding object velocity is larger than object velocities at any other local extremum of the determined focus measures.

18. A system as claimed in claim 16, wherein determining a focus measure comprises determining the focus measure such that the magnitude of the focus measure is independent of the number of objects in each frame.

19. An imaging system comprising:
an imaging device for imaging a liquid sample flowing through a field of view of the imaging device, wherein the imaging device has a focus mechanism for positioning at least a portion of the imaging device in accordance with a focus value to form a focused image of one or more objects in the field of view; and
a processor configured to:
cause the focus mechanism to step through a plurality of focus values while the imaging device captures frames of the sample as the sample flows through the field of view of the imaging device;
segment objects within the sample in the captured frames;
determine a focus measure for each focus value from the captured frames such that the magnitude of the focus measure is independent of the number of objects in each frame;
select one of the plurality of focus values based en the determined focus measures; and
set the focus mechanism using the selected focus value.

20. An imaging system as claimed in claim 19, wherein the processor is configured to refine the selected focus value by setting the focus mechanisms to a plurality of focus values around the selected focus value, determining respective focus measures, selecting a refined focus value based on the respective focus measures and using the refined focus value to set the focus mechanism.

21. An imaging system comprising:
an imaging device for imaging a liquid sample flowing through a field of view of the imaging device, wherein the imaging device has a focus mechanism for positioning at least a portion of the imaging device in accordance with a focus value to form a focused image of one or more objects in the field of view; and
a processor configured to
a) cause stepping of the focus mechanism through a plurality of focus values;
b) acquire at least one video frame at each of the plurality of focus values from the imaging device;
c) calculate a focus measure for each of the plurality of focus values from the respective at least one video frame;
d) select a plurality of respective focus values substantially at local extrema of the focus measure;
e) for each selected focus value, determining a respective object velocity for one or more objects in a respective plurality of frames;
f) select a focus value of the plurality of focus values based on the respective object velocities; and
g) focus the imaging device using the selected value.

22. A system as claimed in claim 21, wherein calculating a focus measure for each focus value includes detecting one or more objects in each respective frame; defining an image patch for each of the one or more objects and calculating the focus measure for at least one of the image patches in each respective frame.

23. A system as claimed in claim 22, wherein calculating a focus measure for each focus value includes averaging the focus measure over objects.

24. A system as claimed in claim 21, wherein step g) comprises:
- h) stepping the focus mechanism of the imaging device through a further plurality of focus values comprising at least one focus value above and at least one focus value below the selected focus value;
- i) acquiring at least one video frame at each of the further plurality of focus values from the imaging device;
- j) calculating a focus measure for each of the further plurality of focus values from the respective at least one video frame;
- k) selecting a further focus value based on the focus measures for the further plurality of focus values; and
- l) focusing the imaging device using the selected further focus value.

25. A system as claimed in claim 24, wherein step l) comprises:
- m) repeating steps a) to k) to select at least one more further focus value;
- n) combining the further focus values to derive a final focus value; and
- o) setting the focus mechanism to the final focus value.

26. A system as claimed in claim 24, wherein a step size between the further plurality of focus values is less than a step size between the plurality of focus values.

27. A system as claimed in claim 21, wherein the sample flows in a microfluidic conduit.

* * * * *

UNITED STATES PATENT AND TRADEMARK OFFICE
CERTIFICATE OF CORRECTION

PATENT NO. : 9,832,366 B2  
APPLICATION NO. : 15/515498  
DATED : November 28, 2017  
INVENTOR(S) : Santos Manso Côrte-Real et al.

It is certified that error appears in the above-identified patent and that said Letters Patent is hereby corrected as shown below:

In the Claims

Claim 4, Column 6, Line 24:
Delete "con tired" and insert -- configured --.

Signed and Sealed this
Twenty-ninth Day of May, 2018

Andrei Iancu
*Director of the United States Patent and Trademark Office*